United States Patent
Mozsary et al.

(10) Patent No.: US 6,258,054 B1
(45) Date of Patent: Jul. 10, 2001

(54) POWER ASSISTED LIPOSUCTION AND LIPOINJECTION EQUIPMENT

(75) Inventors: Peter G. Mozsary, Valley, CA (US); Mike Fard, Charlottesville; John Pascaloff, Keswick, both of VA (US)

(73) Assignee: MicroAire Surgical Instruments, Inc., Charlottesville, VA (US)

( * ) Notice: Subject to any disclaimer, the term of this patent is extended or adjusted under 35 U.S.C. 154(b) by 0 days.

(21) Appl. No.: 09/634,847

(22) Filed: Aug. 8, 2000

Related U.S. Application Data

(60) Continuation of application No. 09/273,768, filed on Mar. 22, 1999, now Pat. No. 6,139,518, which is a division of application No. 08/917,774, filed on Aug. 27, 1997, now Pat. No. 5,911,700, which is a continuation-in-part of application No. 08/814,871, filed on Mar. 11, 1997, now abandoned.

(51) Int. Cl.[7] .................................................. A61B 17/20
(52) U.S. Cl. ................................................................ 604/22
(58) Field of Search ................................... 604/22, 30, 31; 606/169, 171, 30, 31, 35, 43, 50, 118

(56) References Cited

U.S. PATENT DOCUMENTS

| | | |
|---|---|---|
| 2,936,760 | 5/1960 | Gants . |
| 3,082,805 | 3/1963 | Royce . |
| 3,459,175 | 8/1969 | Miller . |
| 3,732,858 | 5/1973 | Banko . |
| 3,734,099 | 5/1973 | Bender et al. . |
| 3,994,297 | 11/1976 | Kopf . |
| 3,995,579 | 12/1976 | Bridgman . |
| 4,077,412 | 3/1978 | Moossun . |
| 4,167,943 | 9/1979 | Banko . |
| 4,167,944 | 9/1979 | Banko . |
| 4,168,707 | 9/1979 | Douvas et al. . |
| 4,203,444 | 5/1980 | Bonnell et al. . |
| 4,311,140 | 1/1982 | Bridgman . |
| 4,314,560 | 2/1982 | Helgott et al. . |
| 4,356,823 | 11/1982 | Jackson . |
| 4,530,356 | 7/1985 | Helgott et al. . |
| 4,536,180 | 8/1985 | Johnson . |
| 4,568,332 | 2/1986 | Shippert . |
| 4,577,629 | 3/1986 | Martinez . |
| 4,589,414 | 5/1986 | Yoshida et al. . |
| 4,627,834 | 12/1986 | Lee . |
| 4,676,780 | 6/1987 | Lee . |
| 4,705,038 | 11/1987 | Sjostrom . |
| 4,713,053 | 12/1987 | Lee . |

(List continued on next page.)

FOREIGN PATENT DOCUMENTS

| | | |
|---|---|---|
| 2622457A | 11/1987 | (FR) . |
| 2648050A | 6/1989 | (FR) . |
| 1255140 | 9/1986 | (SU) . |

*Primary Examiner*—Manuel Mendez
(74) *Attorney, Agent, or Firm*—McGuireWoods LLP

(57) ABSTRACT

A power assisted liposuction/lipoinjection handpiece includes a handle (12) which provides power to reciprocate a cannula (10) back and forth during surgery. The cannula (10) can be connected to the handle (12) by a connector (24) that is affixed to, integrally formed with, or selectively joinable to a reciprocating member (14). Benefits in sterilization, distribution and surgical use can be realized when the cannula (10) and connector (24) are joined together, such that the surgeon merely needs to remove the cannula (10) from the package and connect it to a reciprocating member of a powered handle (12). The handle (12) may be configured such that the reciprocating member (14) is selectively detachable; thereby, allowing the handle (12) to be used for additional surgical procedures such as sawing or drilling. A vacuum hose (26) is connected to the cannula (10) such that vacuum pressure can be exerted through the cannula (10) for aspirating severed fat tissue. Preferably, the connector (24) radially offsets the cannula (10) from the reciprocating member (14) to a position which is axially in alignment with the vacuum hose (26); thereby avoiding bend regions and enhancing suction.

1 Claim, 4 Drawing Sheets

U.S. PATENT DOCUMENTS

| | | |
|---|---|---|
| 4,735,604 | 4/1988 | Watmough et al. . |
| 4,735,605 | 4/1988 | Swartz . |
| 4,770,187 | 9/1988 | Lash et al. . |
| 4,775,365 | 10/1988 | Swartz . |
| 4,792,327 | 12/1988 | Swartz . |
| 4,815,462 | 3/1989 | Clark . |
| 4,834,703 | 5/1989 | Dubrul . |
| 4,838,281 | 6/1989 | Rogers et al. . |
| 4,850,354 | 7/1989 | McGurk Burleson et al. . |
| 4,878,901 | 11/1989 | Sachse . |
| 4,886,491 | 12/1989 | Parisi et al. . |
| 4,919,129 | 4/1990 | Weber, Jr. . |
| 4,923,441 | 5/1990 | Shuler . |
| 4,932,935 | 6/1990 | Swartz . |
| 4,938,743 | 7/1990 | Lee . |
| 4,986,827 | 1/1991 | Akkas et al. . |
| 4,998,919 | 3/1991 | Schnepp-Pesch et al. . |
| 5,000,191 | 3/1991 | Reiss et al. . |
| 5,002,538 | 3/1991 | Johnson . |
| 5,013,300 | 5/1991 | Williams . |
| 5,052,999 | 10/1991 | Klein . |
| 5,076,787 | 12/1991 | Overmyer . |
| 5,112,302 | 5/1992 | Cucin . |
| 5,122,122 | 6/1992 | Allgood . |
| 5,147,316 | 9/1992 | Castillenti . |
| 5,181,907 | 1/1993 | Becker . |
| 5,295,955 | 3/1994 | Rosen et al. . |
| 5,348,535 | 9/1994 | Cucin . |
| 5,352,194 | 10/1994 | Greco et al. . |
| 5,403,276 | 4/1995 | Schechter et al. . |
| 5,411,513 | 5/1995 | Ireland et al. . |
| 5,419,761 | 5/1995 | Narayanan et al. . |
| 5,490,860 | 2/1996 | Middle et al. . |
| 5,569,178 | 10/1996 | Henley . |

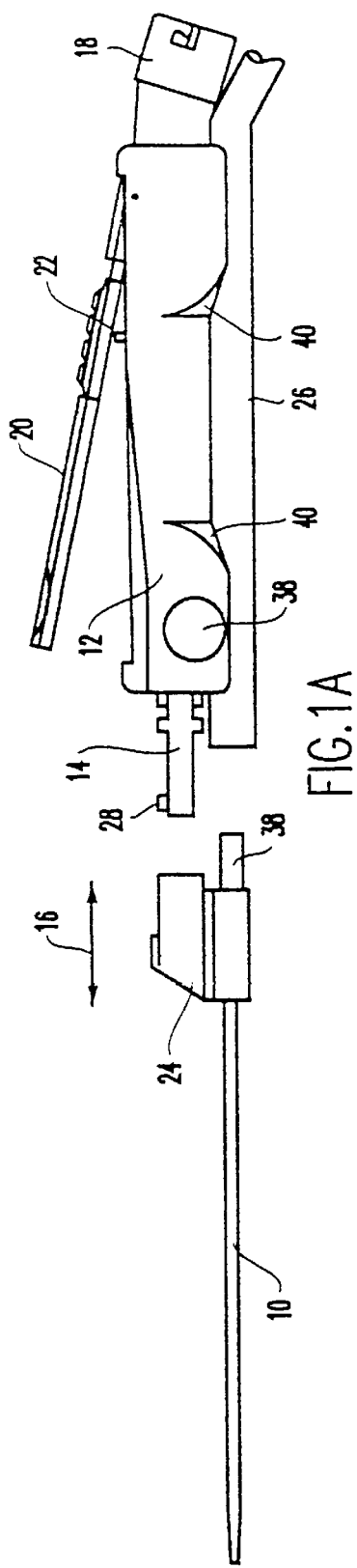
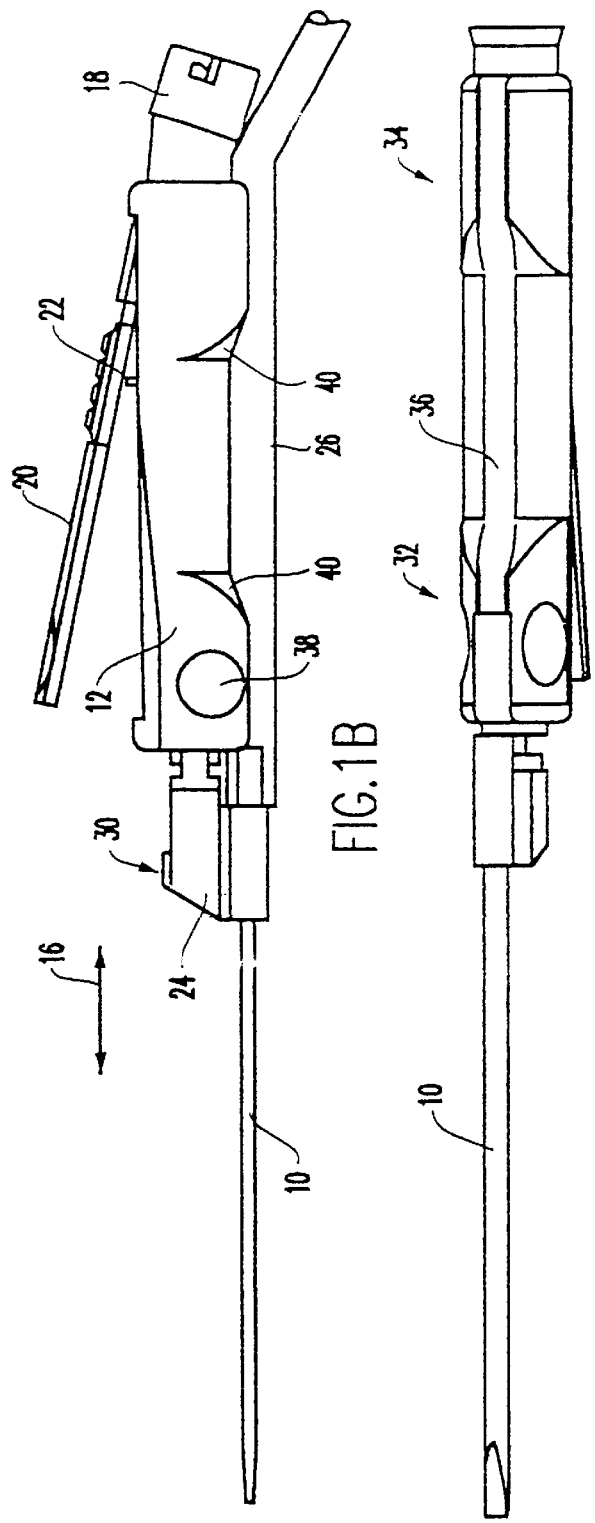

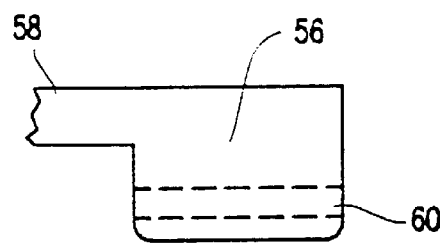
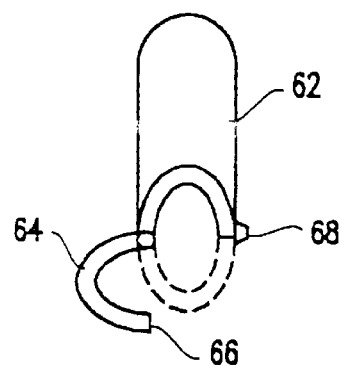
FIG.6  FIG.7
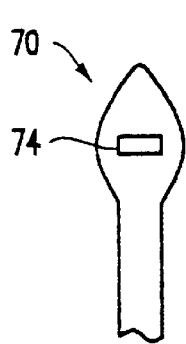 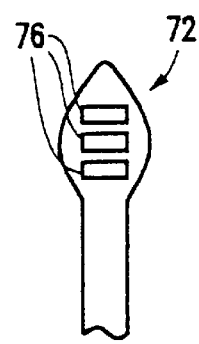 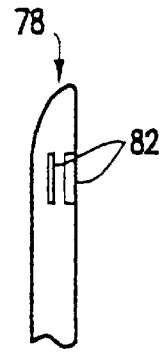 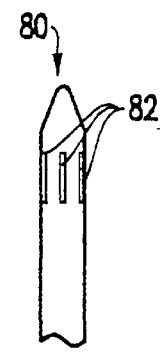
FIG.8A  FIG.8B  FIG.8C  FIG.8D
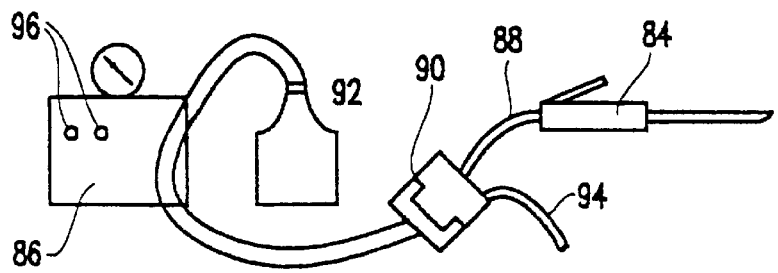
FIG.9
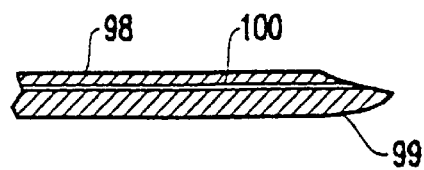
FIG.10

POWER ASSISTED LIPOSUCTION AND LIPOINJECTION EQUIPMENT

CROSS-REFERENCE TO RELATED APPLICATIONS

This patent application is a continuation of U.S. Ser. No. 09/273,768, filed in Mar. 22, 1999, now U.S. Pat. No. 6,139,518, which is a Divisional of U.S. Ser. No. 08/917,774 filed in Aug. 27, 1997, now U.S. Pat. No. 5,911,700, which is a continuation-in-part (CIP) application of the patent application U.S. Ser. No. 08/814,871 filed Mar. 11, 1997, now Abandoned; the complete contents of that application are herein incorporated by reference.

BACKGROUND OF THE INVENTION

1. Field of the Invention

The invention is generally related to powered hand tools used in surgical operations and, more particularly, to hand tools used in liposuction and lipoinjection procedures.

2. Background Description

Liposuction is a well known surgical procedure for surgically removing fat tissue from selected portions of a patient's body. Current practice is to make an incision and then insert a cannula in the space occupied by fat tissue. The cannula is then moved in such a manner as to mechanically break up the fat tissue. While moving the cannula, pieces of the fat tissue are aspirated from the space through the cannula by vacuum pressure from a syringe or pump. This technique requires significant effort on the part of the surgeon in terms of both the physical effort required to move the cannula back and forth, and the effort required to control the direction of movement of the cannula in order for fat tissue to be withdrawn only from specific areas of the patient's body. It would be advantageous to provide equipment which reduces the physical demands on the surgeon, and allows easier control of the direction of cannula movement.

U.S. Pat. No. 4,886,491 to Parisi et al. discloses a liposuction tool which utilizes an ultrasonic probe to break up the fat tissue. U.S. Pat. No. 5,295,955 to Rosen discloses a liposuction apparatus which employs microwave energy to soften fat tissue. The disadvantage of both these approaches is that they do not control the direction of liposuction, and can lead to withdrawing fat tissue unevenly, thus producing a lumpy surface upon completion of the surgery.

Swartz discloses, in U.S. Pat. Nos. 4,735,605, 4,775,365, and 4,932,935, power assisted liposuction tools which include an external sheath which houses a rotary driven auger type element. Fat tissue is selectively sheared at an opening in the external sheath by the auger element pulling tissue within the opening and shearing it off at the opening. In one of the designs, Swartz contemplates oscillating the direction of rotation of the auger element. U.S. Pat. No. 4,815,462 to Clark discloses a lipectomy tool which has an inner cannula with a knife edge opening which rotates within an outer cannula. In Clark, fat tissue is drawn by suction into an opening the outer cannula, and is then sheared off by the knife edge of the inner cannula and aspirated to a collection vessel. A disadvantage with each of these Swartz and Clark designs is that they tend to tear the tissue. This can be problematic when working in confined spaces near blood vessels and the like.

U.S. Pat. No. 5,112,302 to Cucin discloses a powered liposuction hand tool that moves a cannula back and forth in a reciprocating manner. Back and forth movement is akin to the movements made be surgeons, and is therefore a marked improvement over the rotary designs of Swartz and Clark. However, the Cucin design is fairly clumsy and requires the cannula and reciprocating mechanism to move within a portion of the hand held base unit.

U.S. Pat. No. 5,352 to Greco et al. describes an automated liposuction device with reciprocating cannula movement that is akin to Cucin's; however, this device relies on a pneumatic cyclinder drive system, with multiple sensors, and a computer controller to adjust and regulate the cannula movement. Overall, the Greco system is complex and subject to a variety of drive control problems, as well as high costs for various elements. In addition, the Greco system is designed to provide cannula stroke lengths which are in excess of 1 cm, which is not ideal in a number of different circumstances.

U.S. Pat. No. 5,348,535 to Cucin discloses another power assisted liposuction instrument similar to that shown in U.S. Pat. No. 5,112,302 to Cucin. The design in U.S. Pat. No. 5,348,535 utilizes movement of an internal sleeve within an external sleeve to shear off fat tissue pulled within an opening in the external sleeve. The design in U.S. Pat. No. 5,348,535 is complex in that it requires multiple sleeves, and the reciprocating movement causes periodic changes in the aspiration aperture. U.S. Pat. No. 4,536,180 to Johnson discloses a surgical system for suction lipolysis which employs an internal or external air conduit which directs airflow at or near the cutting tip of the cannula to enhance fat tissue clearance during aspiration through the cannula. U.S. Pat. No. 5,013,300 to Williams discloses suction lipectomy tool which allows suction control via the surgeons thumb covering and uncovering vent holes in the lipectomy tool housing.

SUMMARY OF THE INVENTION

It is an object of this invention to provide an improved, power-assisted, reciprocating liposuction tool which overcomes the problems of the prior art and provides a design that is simple in construction, and which provides improved control in the direction and accuracy of fat removal (i.e., eliminates "bumpiness" at the edges of the operated areas; makes it possible to easily remove small patches on the neck, etc.).

It is another object of this invention to provide a hand held, power liposuction tool which drives an external cannula, and which has a form fitting configuration for the surgeon's hand which allows neat storage and selective disengagement of the aspiration tubing, ease in monitoring clogging in the aspiration tube, and simple and direct control of the cannula drive speed.

It is yet another object of this invention to provide power-assisted liposuction tool wherein the forward and rearward stroke length of the cannula cam be set tp be equal to or greater than the size of the cutting window or windows in the cannula.

It is still another object of this invention to provide for the selective connection of disposable and/or reusable cannulas to a power assisted liposuction tool, and to provide for the use of cannulas having a variety of configurations including bullet nosed, spatula tipped, and blunt tipped, each of which may have a single or multiple cutting windows.

It is yet another object of this invention provide a power assisted, reciprocating cutting tool with a suction control feature which allows for adjusting the cutting and aspiration conditions for different tissues.

It is still another object of this invention to provide for a filtering system to be used in conjunction with a power assisted liposuction tool which retains aspirated fat tissue for ease in washing and re-use in lipoinjection procedures.

According to the invention, a powered surgical handpiece includes a reciprocating member to which a cannula is connected. The handpiece drives the cannula back and forth under the control of a drive mechanism that preferably provides for variable speeds of reciprocation. The hand piece can employ any type of drive mechanism; however, a pneumatic, variable speed drive is preferred. In the preferred embodiment, cannulas are connected external to the hand piece by a connector which secures the cannula to a reciprocating member. The connector can either be integral with the cannula, integral with the reciprocating member or constitute a piece which is separate from and connectable to each of the reciprocating member and the cannula. In the most preferred embodiment, the connector is separate from the reciprocating member, and is designed to quickly connect to and disconnect from the reciprocating member by a pushbutton fitting or similar device.

In the preferred configuration, the connector spaces the cannula radially from the axis of the reciprocating member such that the when the cannula is installed, it moves in a reciprocating motion along an axis that is parallel to the axis of the reciprocating member. The offset thus created allows the cannula to be positioned in alignment with a vacuum hose or other vacuum mechanism, such that fat tissue will be freely aspirated through the cannula into the vacuum tube. In the most preferred configuration, the vacuum hose fits directly onto the end of the cannula.

The vacuum hose can be securely connected to the handpiece housing by one or more slot members positioned on the housing. Hence, a surgeon can simply press-fit the hose into the slots on the hand piece, and then secure the hose end to a projection on the connector. Because the hose is made of an elastic material, such as polyvinylchloride, the hose can axially stretch and contract with each reciprocating movement of the cannula/connector combination without narrowing the passage in the hose to a point where vacuum pressure cannot be exerted, and without causing the hose to slip from the slot members. By using an optically clear hose material, the surgeon will be permitted to see when clogs from aspirated fat material occur, so that corrective measures can be taken.

In a preferred embodiment, a filter can be fitted onto the hose such that fat tissue aspirated from the patient's body is collected during the liposuction procedure. Wash fluid can then be directed over the collected fat tissue for washing blood and other extraneous material from the fat, preferably using the same hose and filter. Thereafter, the washed and cleaned fat tissue can then be directed back to the handpiece and used for lipoinjection procedures.

If it is desired to use the handpiece as a power source for a variety of different surgical tools, the reciprocating member can be constructed so as to be removable from the drive mechanism, thus allowing other devices such as saw blades, drill bits, etc. to be connected to the drive mechanism.

The power assisted liposuction tool of this invention is intended to supplement the movements currently used in liposuction procedures, and not as a complete replacement. That is, it has been found that the reciprocal movements of the cannula, which are preferably 0.1 to 6 mm in length, tend to make it significantly easier for the surgeon to move the cannula back and forth in the same manner as is done with a non-power assisted liposuction tool. The precise reason for the reduction in force required is not known but may be related to enhanced fat bursting attributed to the head of the cannula and window sections being moved into and across the fat cells in a repetitive motion while the cannula is being manually moved forward and rearward by the surgeon. In the preferred embodiment, the invention will allow regulation of the suction pressure applied and/or the stroke length of the cannula (i.e., the distance the cannula tip travels from its fully extended to fully retracted positions in one reciprocal motion). In this way, the tool can be used for excising different types of tissue and for working on different types of body fat. For example, it will be understood by one of ordinary skill in the art that the requirements of a liposuction tool in the neck region are different from those in the abdomen and/or legs. The liposuction handpiece of the present invention can be designed to allow for the interchange of cannulas using the same handpiece, the regulation of reciprocation speed, the regulation of suction, and the regulation of stroke length, thereby allowing the same tool to be used in a variety of applications and to meet the needs and desires of several different specialists.

BRIEF DESCRIPTION OF THE DRAWINGS

The foregoing and other objects, aspects and advantages will be better understood from the following detailed description of the preferred embodiments of the invention with reference to the drawings, in which:

FIGS. 1a–b are side views of a power assisted, liposuction/lipoinjection tool according to the present invention respectively showing a cannula disconnected and connected to a reciprocating member of the handpiece;

FIG. 2 is a bottom plan view of the power assisted liposuction/lipoinjection tool showing hose clamping slots formed in the handle region;

FIG. 6 is a side view of a connector which is integral with a receiprocating member and which is selectively connectable to and disengagable from disposable or re-usable cannulas;

FIG. 7 is an end view of a connector which can selectively connect different cannulas;

FIGS. 8a–d are plan views of several different cannula tips showing a variety of different window configurations;

FIG. 9 is a schematic of the liposuction/lipoinjection equipment showing collection of fat tissue in a filter, and suction control;

FIG. 10 is a schematic cross-sectional view of a cannula with an internal fluid or gas delivery tube.

DETAILED DESCRIPTION OF THE PREFERRED EMBODIMENTS OF THE INVENTION

Figure 3:
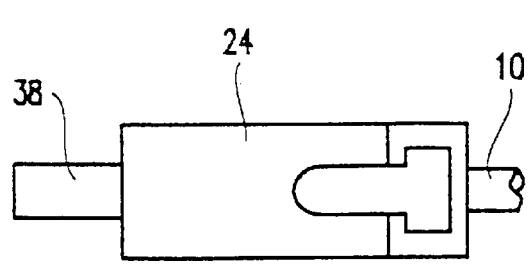
FIG. 3 is a top view of a cannula connector.

FIGS. 1a and 1b show the preferred embodiment of the power assisted liposuction/lipoinjection handpiece of the present invention. A cannula 10 is selectively connectable and disconnectable from a handle 12. The handle 12 includes a reciprocating member 14 which moves back and forth, as indicated by double headed arrow 16, in a reciprocating motion. In the preferred embodiment, the handle 12 includes a pneumatic drive assembly (not shown) and is connectable to a compressed air source by connector 18. An example of a suitable handle with internal pneumatic drive could be the MicroAire® 1400-100. However, it should be understood that any drive mechanism, including electrical, magnetic, etc., can be used to move the cannula 10 in a reciprocating motion 16.

The speed of reciprocation is preferably variable under the control of a lever 20 actuated button or switch 22, whereby complete depression of the lever 20 accelerates the reciprocation to its maximum speed, and partial depression of the lever 20 accelerates the reciprocation to speeds which are less than maximum speed. This enables the surgeon to adjust the speed as conditions require. However, it will be apparent to those skilled in the art that the liposuction tool could employ a simple on/off switch with a preset speed of reciprocation, or a series of pre-set speed buttons which allow the surgeon to selectively alter the reciprocation speed to any pre-established level. The optimum speed of reciprocation 16 may vary for different liposuction operations and/or from patient to patient. It is expected that for most liposuction operations, a maximum speed ranging from 10–100,000 cycles/minute will be suitable. While not shown, the handle 12 could be equipped with sensors and protection circuits which sense the speed of reciprocation 16, and prevent the speed from exceeding a pre-set level, where the pre-set level could be established to protect either the patient or drive mechanism inside the handle 12.

While FIGS. 1a and 1b show a "wand" style handle 12, it will be understood by those of skill in the art that the configuration of the handle can vary widely to meet the needs or desires of the surgeon. Thus, the handle 12 could take the form of a pistol grip or other configuration, and the lever 22 could take the form of a trigger or other suitable mechanism. In the preferred embodiment, the stoke length, which is defined as the difference between the furthest point to which the cannula 10 extends and the shortest point cannula 10 extends in one reciprocating movement 16, will preferably be greater than 0.1 mm and less than 1 cm. The preferred range in most applications will be 1–6 m, and the most preferred is 1–3 mm. While the reciprocating motion 16 itself will allow for breaking up fat particles and aspiration of fat, it is expected that the surgeon will still move the cannula 10 back and forth, or in any other direction, during the liposuction procedure; thereby removing fat from areas he or she deems most appropriate. The reciprocating motion 16 enhances the surgeon's ability to move the cannula 10 after it has been inserted into the patient. When the cannula 10 is being reciprocated by a powered mechanism, particularly for short lengths of less than 1 cm, it is physically easier for the surgeon to move the cannula 10 through material to be aspirated. In this sense, the present invention is intended to supplement the motions and procedures currently used by surgeons in liposuction procedures by making them easier and less tiring to perform, not to replace them. However, for certain procedures, the reciprocating movement 16 might serve as a complete replacement for back and forth movements made by the surgeon.

While not specifically shown in FIGS. 1a–b, a switch or dial or other suitable control structure may be associated with the handle 12 to allow the surgeon to change the stroke length for the cannula to meet his or her requirements for different applications. This control structure would then limit the movement of reciprocating member 14 to desired distance.

In the preferred embodiment, a connector 24 or other suitable device, secures the cannula 10 to the reciprocating member 14 and to a vacuum hose 26 or other suitable source of vacuum pressure. Preferably, a push-button 28 or other selectively actuatable member on the reciprocating member 14 will be used to install and lock the connector 24 to the reciprocating member 14, such that the cannula 10 will be safely retained on the handle 12 during liposuction. Push-button 28 is depressed as it enters a bore passage in the connector 24, and when the connector is correctly installed the push-button returns to the upright position and is locked within a locking region 30 of the connector 24. To remove the cannula 10, the surgeon simply depresses the push-button 28, and slides the connector 24 off the reciprocating member 14. The connector 24 and its installation on the reciprocating member are discussed in more detail below in conjunction with FIGS. 3–5. It should be understood that other locking mechanisms besides push-buttons 28 could be used within the practice of this invention, including for example latch mechanisms, pin mechanisms, and the like.

FIG. 2 shows that in the preferred embodiment, the vacuum hose 26 is secured to the handle 12 via hose clamping slots 32 and 34 formed on the base of the handle 24. The hose clamping slots 32 and 34 are open at the base so that the vacuum hose can be press-fit in place on the bottom of the handle 24 along region 36. This allows the surgeon's hand to comfortably hold the handle 12 without becoming entangled with the hose 26, and assures that the hose 26 remains firmly in place during operation of the liposuction/lipoinjection equipment. To enhance the ergonomics of the handle 12, cut-out spheres 38, and countours 40 can be provided.

To allow aspiration of fat tissue from the cannula, the vacuum hose 26 is fitted onto hose engaging member 38 at the rear of cannula 10 (or, alternatively a projection on the connector 24). The hose engaging member 38 preferably takes the form of a hollow cylinder or a polygonal conduit which is wider in cross-section than the portion of the cannula 10 which is extended into the patient; however, it may be desirable to simply have the hose engaging member 38 simply be the end of the cannula 10. All that is required is that the hose 26 fit onto the hose engaging member 38 and be securely held thereto.

It should be understood that the hose engaging member 38 can either be part of the connector 24 or be part of the cannula 10. In the embodiment where the hose engaging member 38 is part of the connector 24, a passage (not shown) through the connector 24 allows vacuum communication between the cannula 10 and the hose 26. However, it is the preferred embodiment that the cannula 10 be directly connectable to the hose 26. In the configuration shown in FIGS. 1a–b, the cannula 10 extends through the connector 24 and its base would be the hose engaging member 38, and the thickness of the base would, if desired, be widened or made polygonal so that it fits snugly within the internal diameter of the hose.

The vacuum hose 26 will preferably be optically clear, thus allowing the surgeon to determine if the hose 26 is clogged with fat tissue aspirated from the patient's body through the cannula. By monitoring the vacuum pressure and hose line, the surgeon can determine when corrective measures need to be taken during liposuction. Polyvinyl-chloride is an example of a suitable material for the hose 26. The chief requirements for the hose 26 is that it be flexible enough that it be able to be press-fit within and retained by the hose clamping slots 32 and 34, it be sufficiently "stretchable", "pliable" or the like, that it can stretch with reciprocating movements 16 of the cannula without being released from the hose engaging member 38, and have a sufficient internal diameter (not shown) to allow fat tissue and fluids aspirated from the patient's body to flow to a collection vessel or filter.

The design shown in FIGS. 1a and 1b shows the preferred embodiment of this invention where the cannula 10 is offset radially from the axis of the reciprocating member 14 such that it is in direct alignment with the vacuum hose 26. Thus, the cannula 10 reciprocates along an axis which is parallel to the reciprocating member 14, but which is in alignment with the section of the vacuum hose 10 affixed to the handle 12. Alignment of the cannula 10 and vacuum hose 26 eliminates bent regions and, thereby enhances the ability of vacuum pressure to aspirate fat tissue through the cannula 10 into the vacuum hose 26. Furthermore, the alignment makes it easier for the vacuum hose to remain affixed during reciprocation of the cannula 10, as well as making it simpler to affix the connector 24 to the reciprocating member 14 and hose 26.

While the design in FIGS. 1a and 1b provides for neat storage of the hose 26, in some applications it may be desired to have the hose 26 more directly clamped to the cannula (e.g., by a hose clamp or other suitable device), and be freely moveable therewith. In this embodiment, the hose 26 would simply not be stowed under the handle 12 as shown, or, if the invention took the form of a pistol grip design the hose would simply project Off to one side or be oriented in any other convenient manner which preferably does not interfere with the surgical operations being performed.

Having the cannula 10 disconnectable from the reciprocating member 14 provides advantages in terms of cleaning and or disposal; however, it should be understood that more permanent connections can be made. In some applications the cannula might be directly connected to the handle 12, such as by a connection of the cannula 10 directly to a reciprocating drive mechanism, rather than to an intermediate reciprocating member 14.

FIGS. 1a and 1b show a preferred embodiment of the invention where the cannula 10 and connector 24 are be more or less permanently joined together. That is, they are integral such that the cannula 10/connector 24 combination form a self-contained unit which can be selectively installed on the handle 12. In this way, the cannula 10/connector 24 can be sterilized together, and packaged in tubes or sterile packages for later shipment and use. Thus, when required by the surgeon, the package will be opened in the operating room and cannula 10 will be connected to the handle 10 in one step. The cannula 10 and connector 24 can be made from the same or different materials. In the preferred embodiment the cannula 10 is a hollow metal tube and the connector is made from plastic. The cannula 10 and connector 24 can be permanently bonded together by an adhesive to create an integral structure, or simply be connected by a friction fit.

Figure 4:
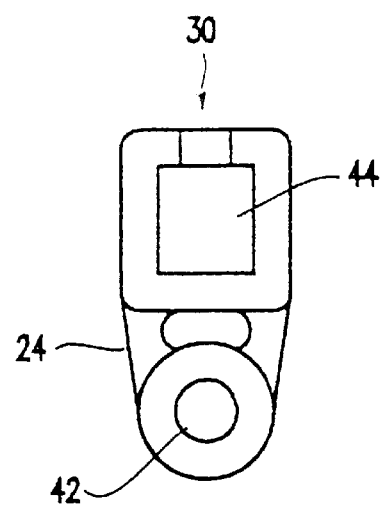
FIG. 4 is a cross-sectional view of a cannula connector.
Figure 5:
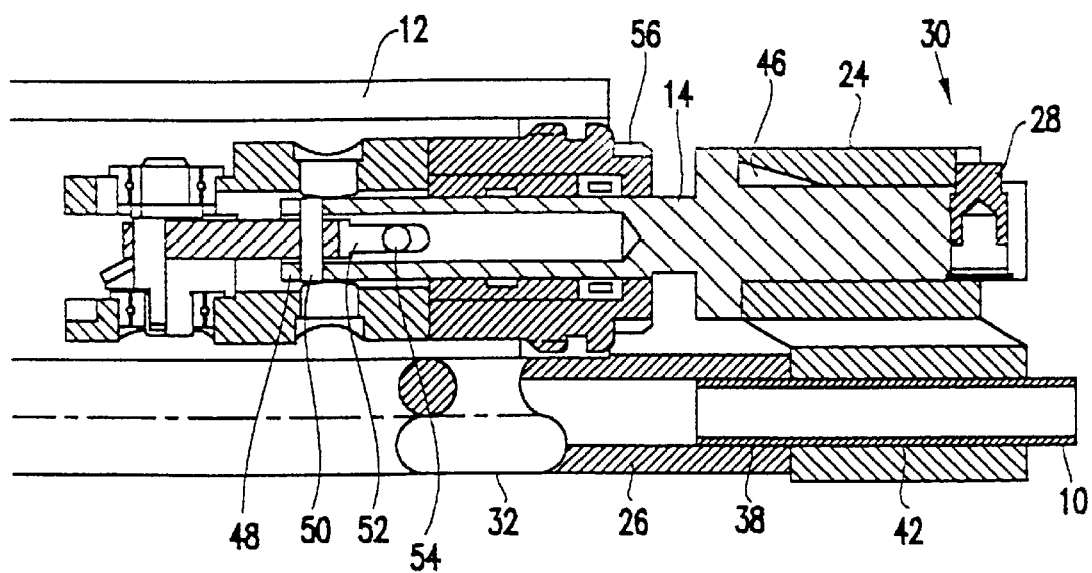
FIG. 5 is a cut-away cross-sectional view of a portion of a connector affixed to a reciprocating member of the handpiece, with a vacuum hose attached to the cannula end.

FIGS. 3–5 show additional details of the preferred embodiment of the invention where the cannula 10 is affixed to a connector 24. In FIG. 3, the hose engaging member 38 at the rear end of the cannula 10 is shown as an enlarged conduit which is either integral with or affixed to the cannula 10. Conversely, in FIG. 5, the rear end of the cannula 10 is not enlarged and the vacuum hose 24 is affixed directly to the base of the cannula 10. In either case, the cannula 10 extends through a cylindrical bore 42 in the connector 24. The vacuum hose 26 is held on the handle 12 by the hose clamping slot 32 shown in partial cross-section, and the inner diameter of the hose 26 is in alignment with the inner diameter of the cannula 10 such that fat tissue broken or sliced off from a patient moves through the cannula 10 into the hose 26 and to a collection vessel. As explained above, the offset provided by the connector 24 assures proper alignment of the hose 25 and cannula 10.

The vacuum hose 26 under the handle 12 preferably does not move in conjunction with the reciprocating motion of the cannula 10 caused by the reciprocating member 14. Rather, the hose 26 could elongate and contract with each reciprocal stroke of the cannula. Alternatively, the cannula 10 could move freely within the inner diameter of the vacuum hose 26. In this case, the stroke length for the cannula 10 would need to be less than the length of the hose engaging end of the cannula 38 protruding from the connector 24, such that the hose remains connected to the cannula at all times. As a further alternative, as discussed above, the hose 24 could be clamped to the hose engaging end 38 of the cannula and could be freely movable therewith; however, this alternative does not take advantage of the neat and clean hose storage feature of this invention.

The connector 24 includes a square bore 44 for connecting with the reciprocating member 14. Making the reciprocating member 14 polygonal in shape assists in preventing the connector 24 from rotating axially about the reciprocating member 14 during high speed reciprocation. To affix the connector 24 on the reciprocating member 14, the reciprocating member 14 is inserted into square bore 44. An incline 46 formed in the connector 24 depresses the pushbutton 28. However, once the pushbutton 28 reaches locking region 30, it moves upward, via a spring mechanism or by other suitable means, and locks the connector 24 onto the reciprocating member 14.

If desired, the reciprocating member 14 could be removed from the handle 12 to allow connecting other tools (e.g., saw blades, drill bits, etc.) to the same handle 12. As indicated above, a suitable powered handle could be the MicroAire® 1400-000 which is used for driving reciprocating saw blades. Thus, if multi-tool functionality is desired, the reciprocating member 14, can be equipped with a drive connecting end 48 that fits on a pin connector 50. The reciprocating member 14 may also have a guide slot 52 which slides on pin guide 54 during reciprocating movements. The reciprocating member 14 would be disconnected by removing securing ring from the front of the handle 12, and then disconnecting the drive connecting end 48 from the pin connector 50. This feature may also be used to connect larger and smaller reciprocating members, or reciprocating members having different shapes to the same handle 12.

With reference back to FIGS. 1a–b, in some applications the cannula 10 could be disconnectable from the connector 24. To aid installation and reduce connecting operations needed by the surgeon, the connector 24 could be formed as an intregal part of the reciprocating member. FIGS. 6 and 7 show alternative designs for a connector where the cannula can be disconnected. By allowing the cannula to be disconnected and connected as desired, the cannula configuration can be very simple (i.e., a hollow tube, preferably made of metal, with one or more cutting windows).

FIG. 6 shows a connector 56 which is integral with a reciprocating portion 58 which is fitted to a reciprocating drive mechanism (not shown). The connector has a bore hole 60 which extends through the length of the connector 56. Cannulas (not shown) can be connected and/or disconnected from the connector 56 by inserting them through the bore hole 60. A friction engagement, which can be supplemented with glue or other adhesives, holds the cannula within the bore hole 60. While connector 56 is shown as being integral with reciprocating portion 58, it should be understood that the same connector 56, which allows for selective attachment and/or disengagement of desired cannulas thereto, could be attachable to a separate reciprocating member 14, as is shown in FIGS. 1a–b.

FIG. 7 shows an alternative embodiment where a connector 62 includes a cannula locking portion 64 which rotates between an open position and a closed position (shown in dashed lines). A cannula (not shown) is inserted in the space between the connector 62 and locking portion 64, and is secured to the connector 62 by shutting the locking portion 64 and securing its free end 66 by a lock 68 or other securing member. To disengage the cannula, the lock 68 is released, and the locking portion 64 of the connector is pivoted away from the connector 62 body.

FIGS. 8a–d show several examples of cannula tips. It should be understood that any type of cannula tip can be used in the practice of the present invention.

FIGS. 8a and 8b show cannulas 70 and 72 with spatula shaped heads. These types of cannulas are preferred in facial surgery and other types of liposuction where there is a need to separate fat from skin and muscle tissue and where space requirements are restricted. The spatula shaped head separates aids in separating the tissues. The face of the spatula shaped head can have a single cutting window 74 or a plurality of cutting windows 76. The shape of the cutting window 74 or 76 can vary to suit the needs of the surgeon. While oval windows are commonly employed, it has been determined that square or rectangular windows 74 and 76 are preferred for spatula shaped heads since they tend to allow for more accurate shaving and sculpting of tissue. In facial surgery, in addition to allowing for aspirating fat tissue from the patient's body, the cutting window 74 or 76 tends to be used to cut tissue from the patients body during each reciprocal motion. Therefore, it is preferred to have the stroke length of the cannula be equal to or larger than the longitudinal distance from the bottom of the cutting window to the top of the cutting window. In this way, each reciprocating stroke of the cannula 70 or 72 will slice off a piece of fat tissue for subsequent aspiration. By keeping the stroke length small (e.g. 1–3 mm) and the longitudinal length of the window 74 or 76 small (e.g., less than or equal to 1–3 mm), fat particles of a small size are excised, and these fat particles are less likely to clog the vacuum hose or cannula.

FIGS. 8c and 8d show cannulas 78 and 80 which are commonly used in full body or abdomen liposuction. FIG. 8c shows a blunt end cannula 78, and FIG. 8d shows a bullet end cannula 80. Each of these cannulas have one or a plurality of windows 82, which are typically oval shaped, around the periphery of the cannula near the tip of the cannula 78 or 80. In this type of liposuction, the reciprocating movement of the cannula 78 or 80, as well as the forward and backward movements of the entire handpiece made by the surgeon, tends to break up fat particles. The fluids and particles which are released from these motions are simply aspirated through the windows 82 in the cannula 78 or 80. In these applications, slicing by the windows 82 may or may not occur.

FIG. 9 shows a reciprocating liposuction tool 84 according to this invention connected to a pump 86 or other vacuum pressure producing device. Fat aspirated through the cannula into the vacuum hose 88 is collected in a filter 90. The filter 90 should have openings which are large enough to allow fluids such as blood, plasma, etc. to pass through, but be small enough to allow larger fat particles to be collected. Preferably the filter 90 can be placed directly in line with the hose 88 or be integral with the hose 88. Fluids including blood pass through the filter 90 and are collected in collection vessel 92.

Collected fat tissue is typically used for lipoinjection procedures. Thus, by collecting the fat from a liposuction operation in a filter 90, the collected fat tissue can be more easily washed and then re-used in a lipoinjection procedure. In order to wash the collected fat, one would only need to remove the filter 90 and run wash or lavage fluids over the fat tissue until blood and other contaminants are removed. The cleaned fat tissue then can be re-injected into the cannula using a delivery hose and other pressure source. In a preferred embodiment, the pump 86 and vacuum hose 88 could be used for both the liposuction and lipoinjection procedures. Cleaned fat tissue would travel down the length of the cannula and would be layered into bores in the patient's body parts made by the surgeon by deposition through the windows 74, 76, or 82. Thus, the use of a collection filter 90 in a liposuction/lipoinjection device provides the advantage of being able to more quickly wash and refuse excised fat tissue. Having the filter 90 in line with the vacuum hose allows the cleaning procedure to be performed immediately after liposuction. Alternatively, a wash line 94 could be connected to the filter 90 to allow cleaning to be performed during liposuction.

The fat collection filter 90 aspect of this invention can be used both with the liposuction/lipoinjection tool described above, and with conventional liposuction tools. All that is required is to provide a filter mechanism which allows isolation of fat tissue from other fluids during liposuction procedures. Prior art systems suffer from requiring a separate washing step to be performed on all of the collected tissue in the collection vessel 92 after the liposuction procedure is completed.

In a particular embodiment of this invention, the pump 86 or other vacuum pressure source could have controls 96 which allow the surgeon to adjust the vacuum pressure exerted at the cannula end. These controls 96 can take the form of dials, switches, buttons, or the like, and are designed to achieve vacuum pressures of varying strength. In most liposuction operations, a vacuum pressure ranging from 70–76 mm Hg is desired. However, greater vacuum pressures may be required if it is desired to use the liposuction tool of this invention in other applications. For example, this tool might also be used for removing bone chips in arthroscopic surgery, or removing cancerous lumps in biopsies, or in other applications. In addition to being able to select the type of cannula desired (e.g., selecting a cannula with large enough windows for cutting and removing cancerous tissue or bones), being able to adjust the vacuum pressure with controls 96 allows for the selective removal of different tissues. For example, at certain vacuum pressures only fat tissue will be aspirated into the windows of the cannula and removed from the patient's body, and surrounding muscle tissue will not be aspirated. However, if a cancerous lesion is desired to be removed, the surgeon would insert the cannula into the lesion and adjust the suction exerted by the pump 86 upward using controls 96.

FIG. 10 shows an embodiment of the invention wherein the cannula 98 includes an internal member 100 which is intended to assist in clearing the cannula 98 of fat tissue aspirated through window 99. Thus, internal member 100 is intended to prevent clogging during liposuction. The internal member 100 can take several different forms. In a preferred embodiment, the internal member 100 delivers a gas (hydrofluorocarbons, oxygen, etc.) or fluid (water, saline, etc.) to the tip of the cannula 98, which, in addition to the vacuum pressure exerted by the pump or other suction device, is intended to help carry the fat tissue down the length of the cannula and into the vacuum hose. To assist in connecting a fluid or gas delivery mechanism to the internal member, the vacuum hose can be fabricated with an internal conduit which carries the fluid or gas to the internal member. In this way, a single connection of the vacuum hose will connect both the cannula and its internal member for both suction and fluid or gas delivery, respectively. While FIG. 10 shows the use of an internal member 100 for fluid or gas delivery, it should be understood that the internal member 100 could also be positioned external to the cannula 98, and be positioned to direct the fluid or gas through the window 99 of the cannula.

In an alternative embodiment, the internal member could be an electrode or similar device which is intended to melt fat material after it is aspirated through window 99. In this application, the internal member 100 could provide microwave energy, ultrasonic waves or heat energy during liposuction.

Figure 11A:
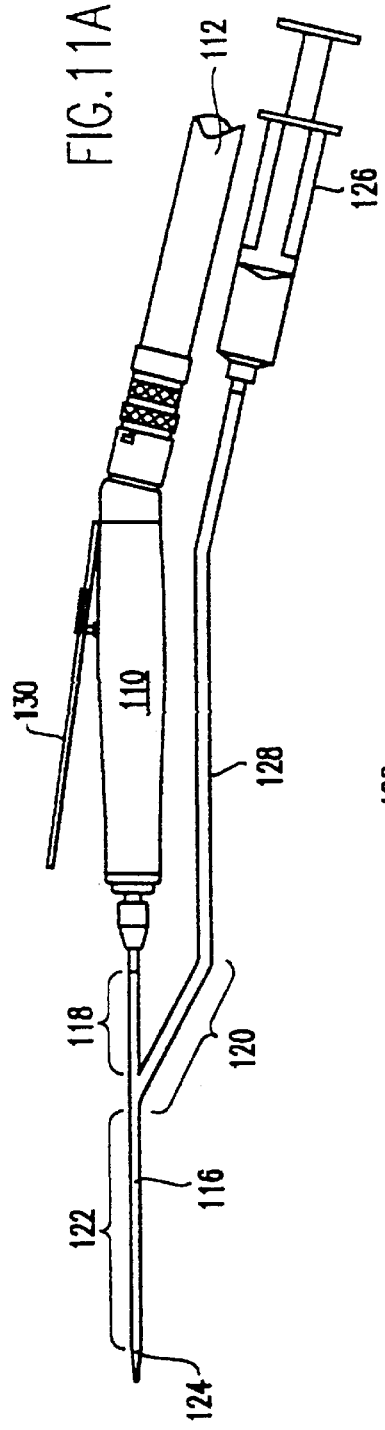
FIGS. 11a–b are side views of alternative power-assisted liposuction handpieces, each having a branched cannula.
Figure 11B:
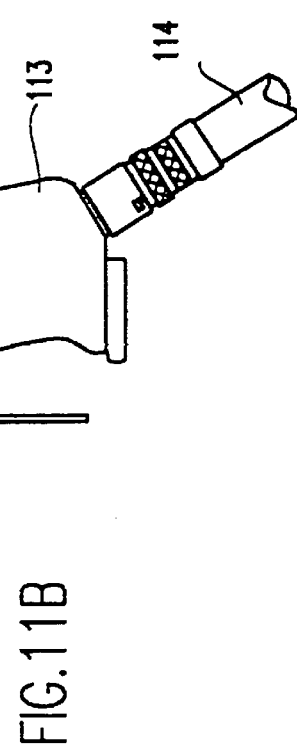

FIGS. 1*a–b* show alternative designs for the power-assisted liposuction handpiece of the present invention, each of which use a "Y" shaped cannula. FIG. 11*a* shows a "wand" style handpiece 110 connected to a pneumatic hose 112, while FIG. 1*b* shows a "pistol grip" style handpiece 113 connected to a pneumatic hose 114. A "Y" shaped cannula 116, having a drive arm region 118, a vacuum branch region 120, and an insertion tip region 122, is connected to the front portion of each handpiece 110 and 113. The tip 124 of the cannula 116 can be narrowed into a point or spatula shape as shown in FIGS. 8*a–b*, or can be blunt ended, bulled shaped, or assume any other configuration desired. Suction from source 126, which can be a syringe, pump, or other suitable device, is directed through vacuum hose 128 to the vacuum branch region 120 and into the insertion tip region 122. As discussed above, the cannula 116 is hollow and allows fat tissue to be withdrawn from the patient into the insertion tip region, through the vacuum branch region and into a collection vessel (not shown), under the pressure exerted by source 126. The drive arm branch 118 is connected to the handpiece 110 or 113 and, as described in detail above, the handpiece 110 or 113 reciprocates the cannula 116 back and forth. Lever 130 or trigger 132 can be used to vary the speed of reciprocation or simply to turn the reciprocating movement on and off. FIGS. 11*a–b* show that the same cannula 116 can be fitted onto different styles of handpieces, and it should be understood that the cannula 10 shown in FIGS. 1*a–b* can also be fitted onto different styles of handpieces in a similar fashion.

While the invention has been described in terms of its preferred embodiments, those skilled in the art will recognize that the invention can be practiced with modification within the spirit and scope of the appended claims.

We claim:

1. A power assisted liposuction handpiece, comprising:
   a housing having a recess substantially along a length of said housing;
   a reciprocating member connecting to said hand held housing;
   a connecting member extending from an end of said reciprocating member;
   a cannula having a hose engaging member and a mating connector mechanism positioned at a rear of said cannula, said mating connector mechanism including an aperture which mates with said connecting member; and
   a vacuum hose fitted onto said hose engaging member at the rear of said cannula and press fitted within said housing.

* * * * *